(12) United States Patent
Bicocchi

(10) Patent No.: US 12,370,540 B2
(45) Date of Patent: Jul. 29, 2025

(54) CONTAINER FOR BIOLOGIC SAMPLES AND METHOD FOR THEIR PRESERVATION

(71) Applicant: Enrico Bicocchi, Leghorn (IT)

(72) Inventor: Enrico Bicocchi, Leghorn (IT)

(*) Notice: Subject to any disclaimer, the term of this patent is extended or adjusted under 35 U.S.C. 154(b) by 677 days.

(21) Appl. No.: 17/756,765

(22) PCT Filed: Dec. 1, 2020

(86) PCT No.: PCT/IB2020/061324
§ 371 (c)(1),
(2) Date: Jun. 1, 2022

(87) PCT Pub. No.: WO2021/111294
PCT Pub. Date: Jun. 10, 2021

(65) Prior Publication Data
US 2023/0010360 A1    Jan. 12, 2023

(30) Foreign Application Priority Data

Dec. 2, 2019 (IT) .......................... 102019000022644

(51) Int. Cl.
*B01L 3/00* (2006.01)
*A61B 10/00* (2006.01)
*A61B 50/00* (2016.01)

(52) U.S. Cl.
CPC ............ *B01L 3/50* (2013.01); *A61B 10/0096* (2013.01); *A61B 2050/0051* (2016.02); *A61B 2050/0066* (2016.02)

(58) Field of Classification Search
CPC .............. B01L 3/50; B01L 2200/0689; B01L 2200/16; B01L 2300/047; B01L 2300/0832; B01L 2400/0683; B01L 3/502; A61B 10/0096; A61B 2050/0051; A61B 2050/0066; A61B 50/00
See application file for complete search history.

(56) References Cited

U.S. PATENT DOCUMENTS 9,442,046 B2 * 9/2016 Biadillah ................ B01L 3/502
11,426,722 B2 * 8/2022 Nguyen .................. B01L 3/502
(Continued)

FOREIGN PATENT DOCUMENTS

| EP | 3220832 A1 | 9/2017 |
| EP | 3328286 B1 | 9/2019 |
| WO | 2021111294 A1 | 6/2021 |

*Primary Examiner* — Samuel P Siefke
(74) *Attorney, Agent, or Firm* — Reches Patents

(57) ABSTRACT

A container (1) for biologic samples has a lower receptacle (2), an upper receptacle (3) for a toxic liquid (LF) or considered as such, having a radial ring (63), and a connecting sleeve (4) with a circumferential rim (54) and a transversal septum (40), provided with a central vent opening (55) and with a plurality of transfer openings (51) for the transfer of toxic liquid (LF). The toxic liquid (LF) is sealed between the upper receptacle (3) and the transversal septum (40) before unscrewing the upper receptacle until its radial ring (63) touches the circumferential rim (54). When unscrewing the upper receptacle (3), the toxic liquid (LF) reaches and passes through the plurality of transfer openings (51), and air contained in the lower receptacle (2) flows into the upper receptacle (3) through the central vent opening (55), without any exit of gases and liquids from the container (1).

12 Claims, 5 Drawing Sheets

(56) References Cited

U.S. PATENT DOCUMENTS

| | | | |
|---|---|---|---|
| 2012/0024861 A1* | 2/2012 | Otsuka | B65D 51/2864 |
| | | | 366/130 |
| 2012/0024862 A1* | 2/2012 | Otsuka | B65D 81/3211 |
| | | | 220/502 |
| 2013/0164738 A1* | 6/2013 | Becker | C12N 15/1006 |
| | | | 435/306.1 |
| 2017/0231604 A1 | 8/2017 | Jakobsen et al. | |
| 2019/0314003 A1 | 10/2019 | Saqi et al. | |

* cited by examiner

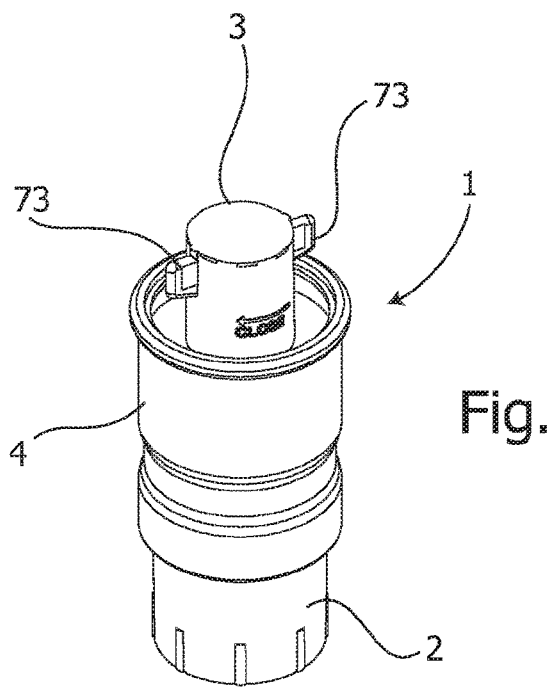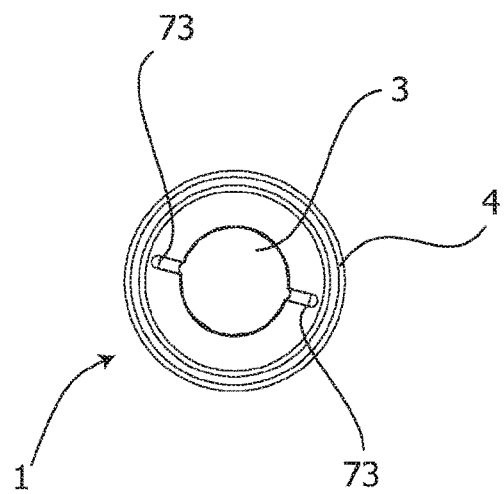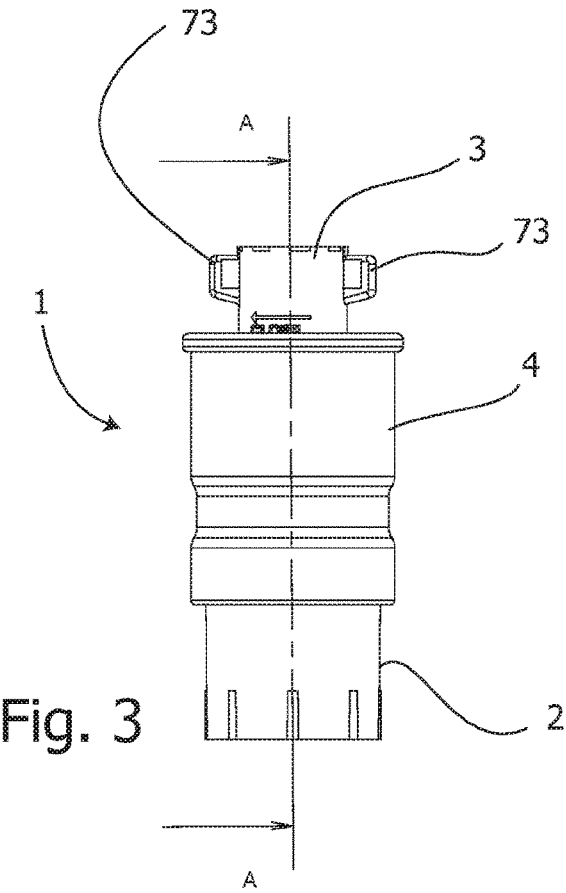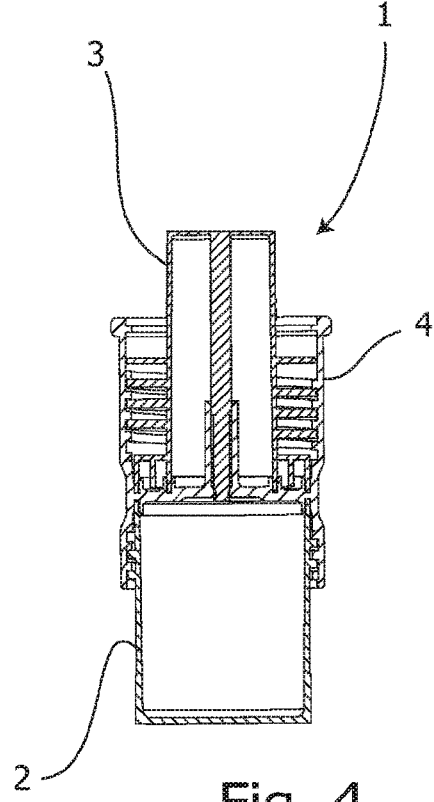

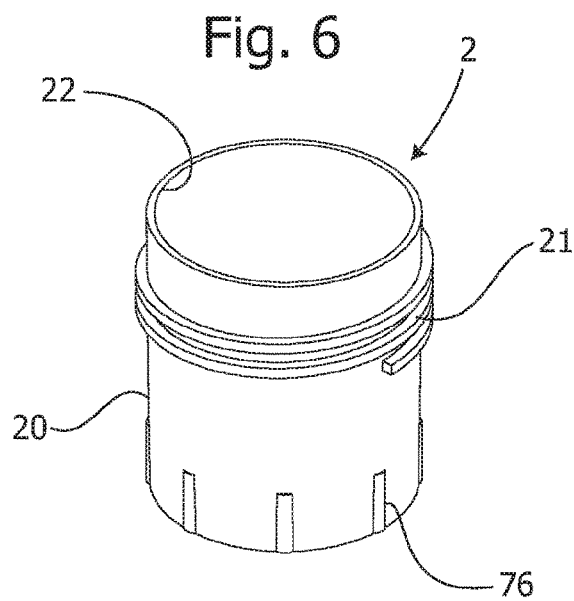
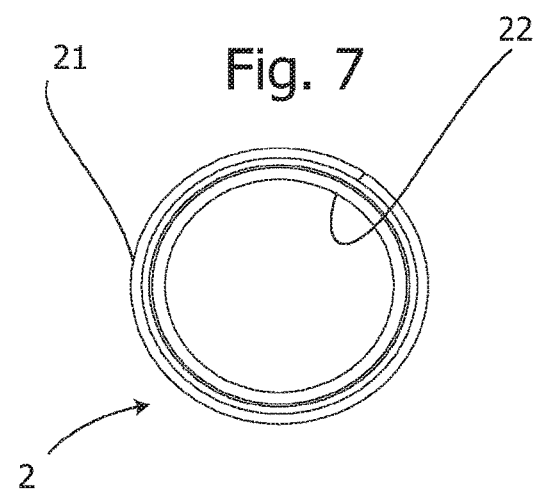
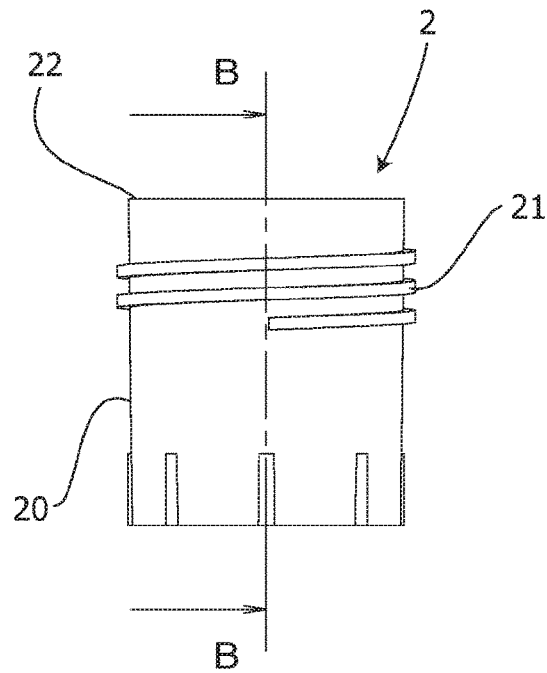
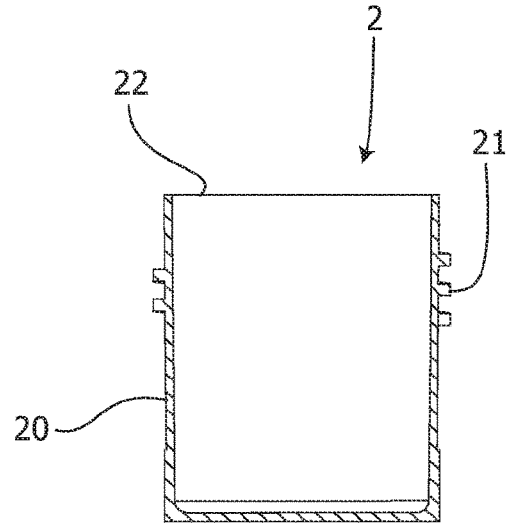

CONTAINER FOR BIOLOGIC SAMPLES AND METHOD FOR THEIR PRESERVATION

TECHNICAL FIELD

The present invention relates to a container for biological samples. In particular, it relates to a container for in vitro diagnostics and research that allows the preservation, storage and transport of biological samples, such as biopsies or surgically removed tissue fragments, or a sample of stool or biological liquid, for example urine, ascites, pleural fluid. The field of application of the invention is, more specifically, that of in vitro tests for diagnostics and research in pathology, histology, microbiology and molecular biology in biological samples. The container is of the disposable type. The invention also relates to a method for the stabilization and preservation of samples of human, animal or plant origin.

BACKGROUND ART

More in detail, biological samples are commonly taken for pathological, histological, microbiological or molecular analysis in order to detect, study, stage and determine the optimal treatment of numerous diseases.

An essential requirement for an accurate and detailed morphological or molecular analysis is the high quality of the biological sample that avoids structural and molecular changes due to exposure of the sample to environmental stress or caused by degradation processes intrinsic to the sample itself. Therefore, it is necessary to provide a container and a method for preserving, immediately after sampling or as soon as possible, and subsequently storing or transporting such biological samples under controlled conditions while maintaining and stabilizing the structural and molecular integrity of the sample. Such preservation and storage are commonly achieved by adding appropriate chemical reagents to the samples.

Traditionally, in cytology and histology to preserve and store cells and tissues, the sample is immersed in a single mixture of preservative/stabilizer reagent. Unfortunately, fluids suitable for this are often toxic or dangerous. For example, 10% neutral buffered formalin, the most commonly used preservative/stabilizer reagent in diagnostic histopathology, is a 4% formaldehyde solution in phosphate isotonic buffer. In the diagnostic routine it is clear that the greatest problem in the use of formaldehyde is the containment of health risks for the operators, since formaldehyde has been classified as a substance with high acute toxicity due to ingestion, skin contact and inhalation. The Commission Regulation (EU) No. 605/2014 classifies formaldehyde as Carc. 1B and Muta. 2 (substance classified as carcinogenic, mutagenic or toxic).

EP3328286 describes a disposable container for the preservation and transport of human tissue samples, comprising a receptacle containing a buffer solution, a piercing cap, a capsule containing formalin sealed by means of a protective film, a safety ring nut inserted between the base of the piercing cap and the capsule. A stopper, positioned on the threading of the ring nut, is broken when the capsule is screwed onto the ring nut.

EP3220832 discloses a container including a body adapted to contain a biopsy sample and a cap adapted to be screwed onto the body to close it tightly. The cap comprises a receptacle for containing a preserving solution closed at the bottom by a tearable membrane, and a puncturing member adapted to be pressed against the membrane to tear it. The cap has a perforated lower wall to allow the preservative solution to flow from the receptacle to the body as a result of tearing of the membrane.

US2017/0231604 discloses a tissue-sample container and a lid. The lid has a sealed receptacle adapted to contain a preserving agent and a puncturing element actuatable to break the seal.

In order to safeguard users from the risks of formaldehyde, WO2019092638 of the same Applicant describes an in vitro diagnostic container having a lower receptacle intended to contain a non-toxic liquid, an upper receptacle intended to contain a toxic liquid, and a connecting sleeve in threaded coupling with the lower receptacle and the upper receptacle for their butt joint. The connecting sleeve has a transversal septum, provided with a plurality of transfer openings and a central vent opening. The lower receptacle and the upper receptacle abut against the transversal septum when the container is completely closed. If the upper receptacle is partially unscrewed from the transverse septum, the toxic liquid passes by gravity into the lower receptacle. In the aforementioned container according to WO2019092638, the tight seal of the upper receptacle against the transversal septum is not guaranteed, due to the simple butt joint of the same. In addition, the transfer of toxic liquid from the upper to the lower receptacle could lead to the entry of a small amount of air from the outside and the consequent leakage to the outside of the same volume of air potentially mixed with vapors from the toxic liquid. In addition, the unscrewing of the upper receptacle with respect to the connecting sleeve is limited by a stop projection provided in the internal thread of the upper part of the connecting sleeve near the upper end of its upper part. In this way, a user should be advised not to proceed by forcing the unscrewing, which could lead to further diffusion of toxic liquid vapors. It is evident that the precaution provided by the retaining protrusion is not sufficient to reduce the risk of contamination.

SUMMARY OF THE INVENTION

The invention aims to overcome the drawbacks presented by the prior art. An object of the present invention is to eliminate the risks of exposure both by contact and by inhalation, to the preservative/stabilizer reagent typically containing toxic or harmful substances during the transfer and deposition of the biological sample in the container for in vitro diagnostics.

A main object of the invention is to provide a container that is easy to use and reliable in creating a tight seal of the upper receptacle against the transversal septum of the connecting sleeve.

A further object of the invention is to avoid the entry of air from the outside when activating the device and the escape of air mixed with vapors coming from the toxic liquid or considered as such.

Yet another object of the invention is to provide an accurate abutment for a safe and reliable unscrewing of the upper receptacle with respect to the connecting sleeve to avoid a further potential source of diffusion of toxic liquid vapors.

Another important object is to provide a method of using the container with the aforementioned purposes that is intuitive and leaves little chance of error to those who work for the storage and transport of a biological sample to be subjected to pathological, histological, microbiological and molecular examinations.

A further object of the invention is to provide a complete and pre-filled container with the reagents, which does not require sealing the toxic liquid with protective films and, therefore, does not present the risk that pieces of film create an obstacle to the flow of the preservative reagent from upper to lower receptacle.

Another object of the invention is to eliminate risks deriving from the possible backflow of liquid from the lower receptacle to the upper receptacle after closing the container.

Therefore, in a first aspect thereof, the present invention provides a container for biological samples according to claims 1 to 10.

In a second aspect thereof, the invention provides a method for storing a biological sample according to claims 11 and 12.

BRIEF DESCRIPTION OF DRAWINGS

Further features and advantages of the invention will become most clear from a description of an embodiment of the container, illustrated in the accompanying drawings in which:

FIGS. 1 to 4 are a general perspective view, a top plan view, a side view and a central longitudinal cross-section along lines A-A in the side view, respectively, of a container according to the present invention, in closed position;

FIGS. 6 to 9 are a perspective view, a top plan view, a side view and a central longitudinal cross-section along lines B-B in the side view, respectively, of a lower receptacle of the container according to the present invention;

DETAILED DESCRIPTION OF AN EMBODIMENT

Figure 5:
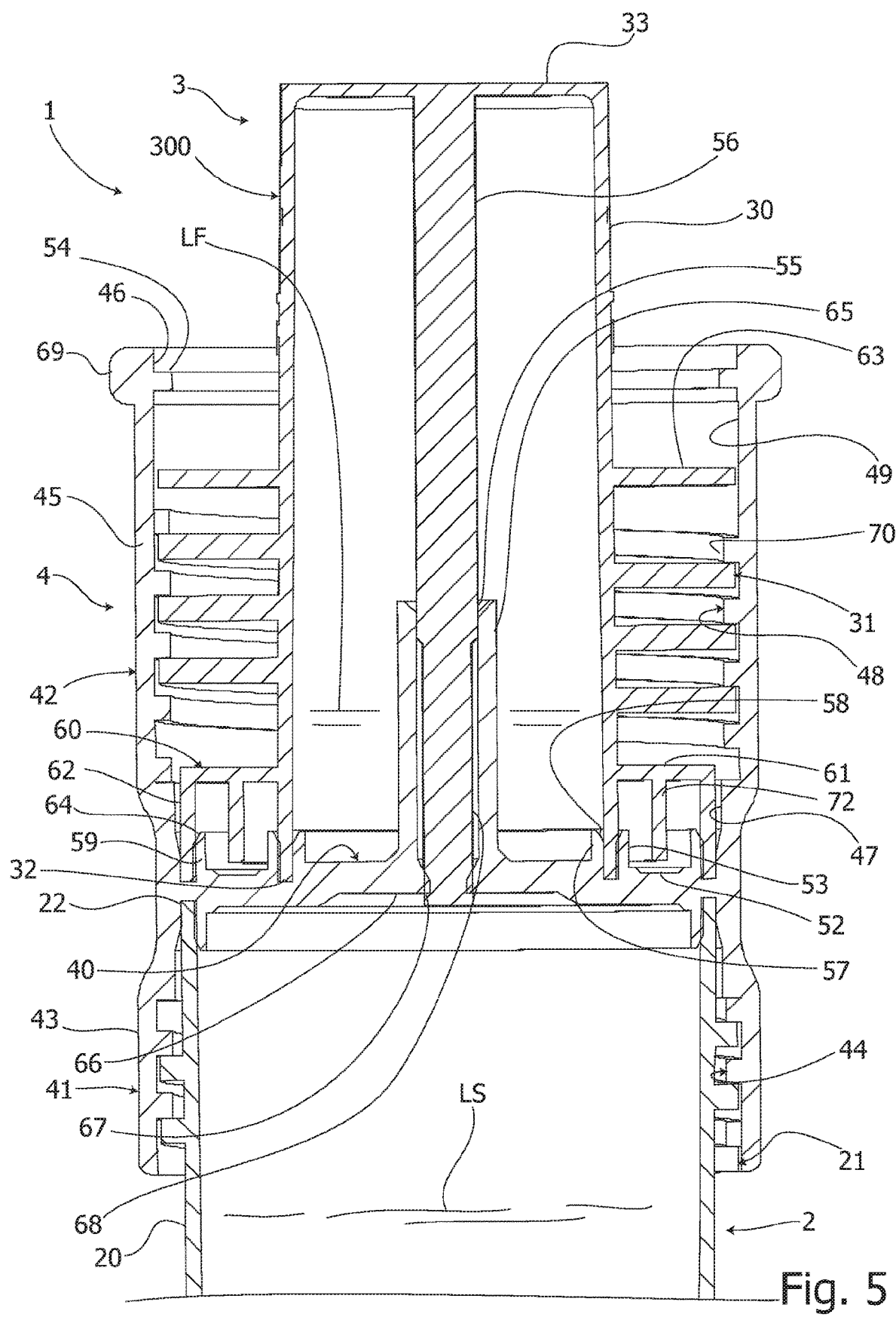
FIG. 5 is a partial enlarged view of the central longitudinal cross-section in FIG. 4.
Figure 10:
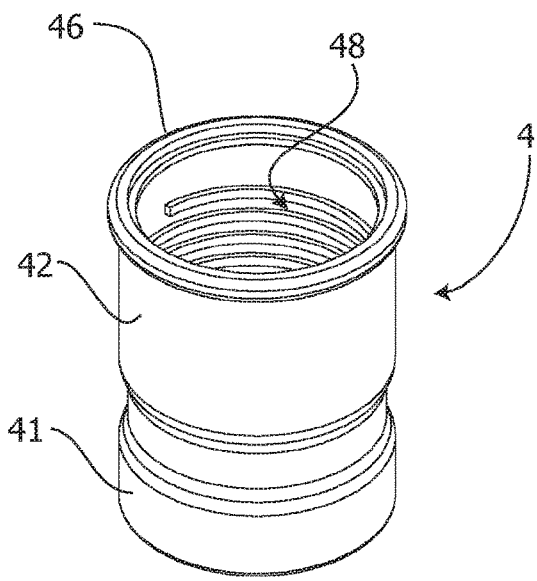
FIGS. 10 to 13 are a perspective view, a top plan view, a side view and a central longitudinal cross-section along lines C-C in the side view, respectively, of a connecting sleeve of the container according to the present invention.
Figure 11:
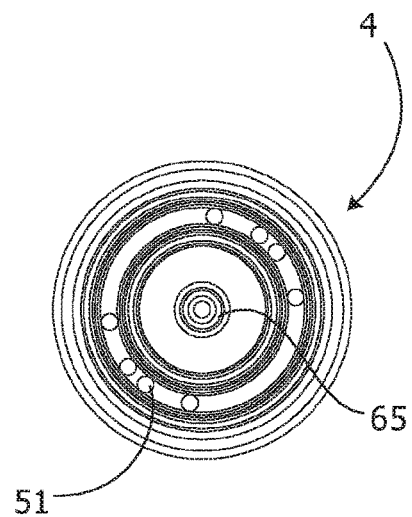
Figure 12:
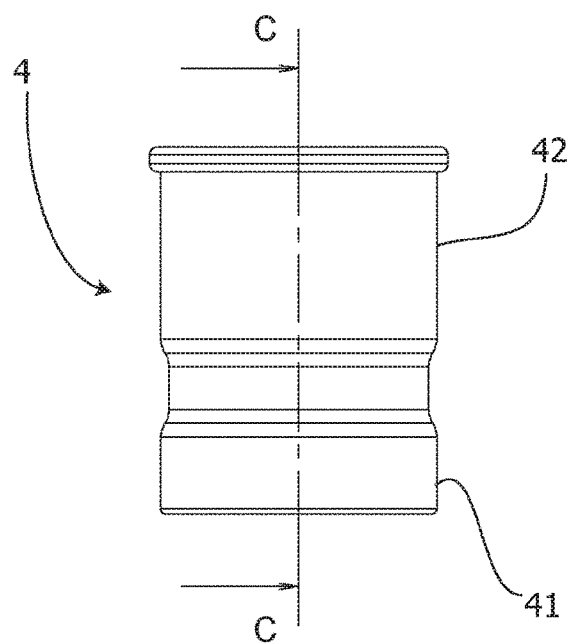
Figure 13:
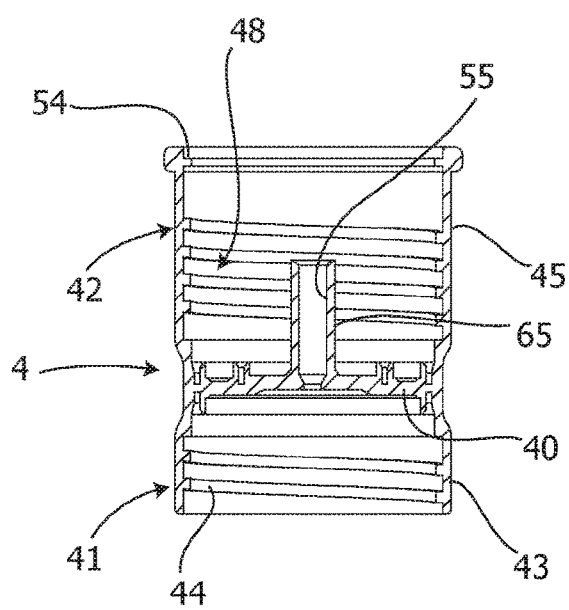
Figure 14:
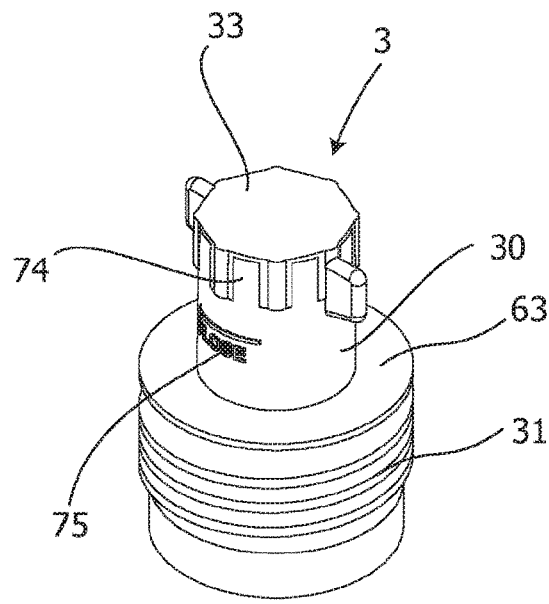
FIGS. 14 to 17 are a perspective view, a bottom plan view, a side view and a central longitudinal cross-section along lines D-D in the side view, respectively, of an upper receptacle of the container according to the present invention.
Figure 15:
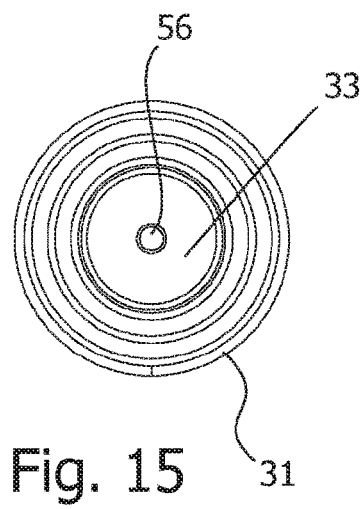
Figure 16:
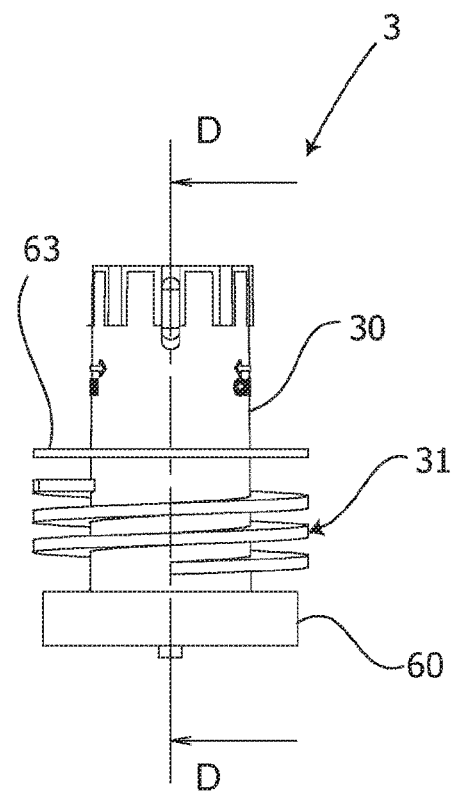
Figure 17:
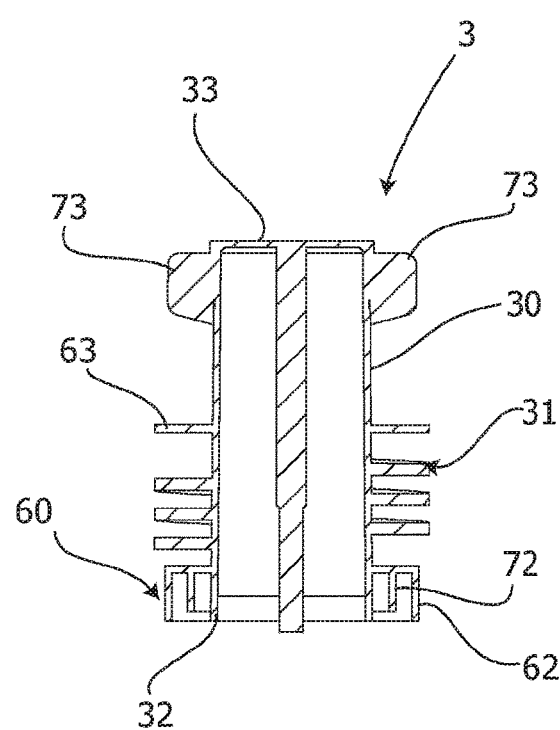

Reference is initially made to FIGS. 1 to 4 which are a general perspective view, a top plan view, a side view and a central longitudinal cross-section, respectively, of the container 1 for in vitro diagnostics according to the present invention, in closed position. The central longitudinal cross-section of FIG. 4 is obtained along the line A-A of FIG. 3.

The container 1 is composed of a lower receptacle 2, an upper receptacle 3 and a connecting sleeve 4, the latter acting as a threaded coupling means for joining the lower receptacle 2 to the upper receptacle 3. The terms "lower" and "upper" refer to the upright position of the container in its handling, because when the container is completely closed it can assume any position without any prejudice.

The lower receptacle 2 is preferably intended to contain, before activating the container, a non-toxic liquid, such as a buffer solution typically adapted to prevent the dehydration of solid samples or to suspend semisolid samples or to dilute liquid samples. It should be evident that the lower receptacle 2 could be without liquid, if the liquid is not required for the specific storage of the biological sample. As shown in FIGS. 6 to 9, which are a perspective view, a top plan view, a side view and a central longitudinal cross-section along the lines B-B in the side view, respectively, of the lower receptacle 2, the latter has a side wall 20 equipped of an external thread 21 and ending with a circular mouth 22.

Reference is now made to FIGS. 14 to 17, which are a perspective view, a bottom plan view, a side view and a central longitudinal cross-section along the lines D-D in the side view, respectively, of the upper receptacle 3 of the container 1 according to the present invention. The upper receptacle 3 is intended to contain, before the activation of the container, a toxic liquid or considered as such, typically a preservative/stabilizer mixture. The upper receptacle 3 has a side wall 30 provided with an external thread 31 and ending with a circular mouth 32.

Reference is now made to FIGS. 10 to 13 which are a perspective view, a top plan view, a side view and a central longitudinal cross-section along the lines C-C in the side view, respectively, of a connecting sleeve 4 of the container 1 according to the present invention. The connecting sleeve 4, as shown in FIG. 4, is longitudinally engaged with the external threads 21 and 31 of the lower receptacle 2 and the upper receptacle 3, respectively, for the butt joint of the same receptacles. The connecting sleeve 4 has a transversal septum 40 against which the lower receptacle 2 and the upper receptacle 3 abut, on opposite sides, with their respective circular mouths 22, 32 when the container 1 is completely closed.

It is therefore understood that the threaded coupling means between the lower receptacle 2 and the upper receptacle 3 according to the invention consist of the single connecting sleeve 4, comprising a lower part 41 and an upper part 42.

The lower part 41 has a side wall 43 with an internal thread 44 engaging with the external thread 21 of the lower receptacle 2. The upper part 42 has a side wall 45 with an internally threaded band 48 engaging with the external thread 31 of the upper receptacle 3.

The transversal septum 40 separates the lower part 41 of the connecting sleeve 4 from its upper part 42 and is provided with a plurality of transfer openings 51 in the form of through holes, provided in a peripheral area 52 of the transversal septum 40, and with a central vent opening 55 of a chimney element 65.

In particular, with reference to FIG. 5, the upper side wall 45 of the upper part 42 of the connecting sleeve 4 includes a first internally smooth band 47, the aforementioned internally threaded band 48 with a thread 70 which engages with the external thread 31 of the upper receptacle 3, and a second internally smooth band 49 near a free end 46 of the upper part 42.

According to the present invention, a tight seal of the upper receptacle 3 against the transverse septum 40 is created thanks to particular configurations made in the coupling of the former with the latter.

In particular, in the side of the transversal septum 40 of the connecting sleeve 4 facing the upper receptacle 3 there is provided a first circumferential projection 53 which protrudes orthogonally in the upper part 42 of the connecting sleeve 4, internally delimiting the peripheral area 52 of the transversal septum 40. The first circumferential projection 53 is adapted to create a tight seal with the circular mouth 32 of the upper receptacle 3 when this is completely screwed into the upper part 42 of the connecting sleeve 4.

Preferably, a second circumferential projection 57, coaxially inside the first circumferential projection 53, protrudes from the transversal septum 40 orthogonally in the upper part 42 of the connecting sleeve 4 so as to form a first groove 58. Conveniently, the first circumferential projection 53 and the second circumferential projections 57 are tapered upwards so as to create a guide for the circular mouth 32 of the upper receptacle 3. In fact, the first groove 58 is adapted to receive this circular mouth 32, creating a seal better than the single first circumferential projection 53. In this way, the toxic liquid LF contained inside the upper receptacle 3 is prevented from escaping from the same when it is completely screwed against the transversal septum 40. Advantageously, always on the side of the transversal septum 40 facing the receptacle 3, there is a third circumferential projection 59 projecting orthogonally and coaxially to the previous first circumferential projection 53 and second circumferential projection 57 in the upper part 42 of the connecting sleeve 4. The third circumferential projection 59 creates a second groove 64 with the first internally smooth band 47 of the connecting sleeve 4 to prevent any toxic liquid that may have leaked from the receptacle 3, through the coupling of the first groove 58 with the circular mouth 32, from dispersing between the upper part 42 of the connecting sleeve 4 and the outside of the upper receptacle 3. This is achieved with a particular configuration of the upper receptacle 3 around its circular mouth 32.

In this particular configuration, the upper receptacle 3 comprises, concentrically to its circular mouth 32, a hollow cylindrical element 60 having a transversal base 61 and a first longitudinal circumferential wall 62 intended to come into lateral hermetically sealed contact with the first internally smooth band 47 of the upper side wall 45 of the connecting sleeve 4.

In particular, the first longitudinal circumferential wall 62 of the hollow cylindrical element 60 of the upper receptacle 3 is inserted in the second groove 64, created by the third circumferential projection 59 with the first internally smooth band 47 of the upper side wall 45 of the connecting sleeve 4.

In order to create a further labyrinth seal between the upper receptacle 3 and the transversal septum 40, the hollow cylindrical element 60 of the upper receptacle 3 comprises, concentrically to the circular mouth 32, a second longitudinal circumferential wall 72 intended to come into contact at the ends with the peripheral area 52 of the transversal septum 40 of the connecting sleeve 4.

This second longitudinal circumferential wall 72, which is coaxial with the first longitudinal circumferential wall 62, prevents the toxic liquid LF if any leaking from the upper receptacle 3 from reaching the first internally smooth band 47 of the upper side wall 45 of the connecting sleeve 4.

The upper side wall 45 of the connecting sleeve 4 has a free end 46 with a circumferential rim 54, at least partial, protruding inwards. The circumferential rim 54, preferably complete, has an internal diameter capable of creating an undercut in the second internally smooth band 49 in the upper part 42 of the connecting sleeve 4. The function of the circumferential rim 54 will be clarified below. At the circumferential rim 54, the sleeve 4 has a bulge 69 protruding outward in its free end 46.

The upper receptacle 3 preferably has a cylindrical body 300 containing the toxic liquid LF with a diameter considerably smaller than that of the upper part 42 of the connecting sleeve 4. This choice determines the fact that its external thread 31, which engages with the thread 70 of the internally threaded band 48 of the connecting sleeve 4, has a significant diameter compared to that of the cylindrical body 300 of the upper receptacle 3. It follows that the external thread 31 of the upper receptacle 3 is sufficiently flexible to allow a forced introduction of the upper receptacle 3 at the upper part 42 of the connecting sleeve 4.

Furthermore, on the cylindrical body 300 there is a radial ring 63, with an external diameter slightly greater than that of the thread 31, as well as greater than the internal diameter of the circumferential rim 54 of the connecting sleeve 4.

The upper receptacle 3 has a closed base 33 from which a stem 56 hangs internally. The stem 56 is able to fit tightly into the central vent opening 55 of the chimney element 65 when the upper receptacle 3 is completely screwed, and to create an air passage when the upper receptacle 3 is partially unscrewed up to said circumferential rim 54.

In the side of the transversal septum 40 opposite to that of the chimney element 65, the transversal septum 40 has a recess 66 into which the central vent opening 55 of the chimney element 65 merges through a narrow port 67.

The stem 56 of the upper receptacle 3, which is able to move in the central vent opening 55 of the chimney element 65 in the screwing and unscrewing of the upper receptacle 3 in the upper part 42 of the connecting sleeve 4, has a terminal tract 68 of reduced diameter compared to that of the rest of the stem 56.

The terminal tract 68 of reduced diameter is designed to ensure a tight seal with the narrow port 67 of the central vent opening 55 in the recess 66 when the upper receptacle 3 is completely screwed into the upper part 42 of the connecting sleeve 4.

The terminal tract 68 of the stem 56 provides an air passage when the upper receptacle 3 is unscrewed in the upper part 42 of the connecting sleeve 4 up to the circumferential rim 54.

The upper receptacle 3 has two opposite external radial fins 73 to facilitate the grip and rotation of the upper receptacle 3. The same function has the prismatic configuration with a polygonal plan with rounded corners 74 obtained on the body 300 of the upper receptacle 3. Marked on this with 75 are arrows or word to indicate the direction of closure and opening, respectively, of the upper receptacle 3. It will be understood that certainly the direction of opening is most critical for safety purposes.

Projections 76 are provided in the wall 20 of the lower receptacle 2 to facilitate its unscrewing and screwing.

The present invention also provides a method for storing a biological sample, of human, animal or vegetable derivation, with the use of the container for in vitro diagnostics described so far. Starting from a completely closed and sealed container, already provided with the non-toxic liquid LS and the toxic liquid LF, in the receptacles 2 and 3 respectively, the method comprises the steps of completely unscrewing the lower receptacle 2 containing the non-toxic liquid LS from the connecting sleeve 4, direct introduction of the sample inside the lower receptacle 2, and screwing the lower receptacle 2 onto the connecting sleeve 4 in such a way as to obtain a tight seal. These steps are those already provided for in the method disclosed in WO2019092638.

According to the present invention, following the steps listed above is the unscrewing of the upper receptacle 3 until its radial ring 63 comes into contact with the circumferential rim 54 of the connecting sleeve 4. In this way, the toxic liquid LF is poured from the container by gravity 3 where it is located at a height lower than that of the chimney element 65 up to the peripheral area 52 of the transversal septum 40, where is the plurality of transfer openings 51. Hence, the toxic liquid LF passes through the transfer openings 51 thanks to the fact that the air contained in the lower receptacle 2 above the non-toxic liquid with the immersed sample passes through the vent opening 55 of the chimney element 65 to move into the upper receptacle 3. The mixture of air and vapors of toxic liquid LF could reach the hollow cylindrical element 60, but it cannot rise along the first longitudinal circumferential wall 62 which is in lateral contact with tight seal with the first internally smooth band 47 of the upper side wall 45 of the connecting sleeve 4. If the mixture of air and vapors of toxic liquid LF reached the threaded coupling area between the thread 31 of the upper receptacle 3 and the internally threaded band 48 of the connecting sleeve 4, the mixture of air and vapors of toxic liquid LF could not continue towards the outside of the connecting sleeve 4 because the radial ring 63 of the upper receptacle 3 closes the passage by abutting from the inside the circumferential rim 54 of the same connecting sleeve 4.

After the complete transfer of the toxic liquid LF into the lower receptacle 2 has taken place, the upper receptacle 3 is screwed back against the circular mouth 32 on the transversal septum 40.

In this way, before the activation of the container 1, the toxic liquid LF is confined in a space delimited by the upper receptacle 3 and the transversal septum 40, against which the upper receptacle 3 is completely screwed into the upper part 42 of the connecting sleeve 4. During activation, with the unscrewing of the upper receptacle 3, there is no communication between the interior of the container 1 and the outside, and after activation, the container 1 is closed again by screwing the upper receptacle against the transversal septum 40 of the connecting sleeve 4.

In the latter condition, the position of the parts existing before the activation of the container is restored. That is to say, the upper receptacle 3 is again sealed with respect to the lower receptacle 2 because its circular mouth 32 is hermetically sealed against the transversal septum 40 of the connecting sleeve 4; the central vent opening 55 of the chimney element 65 is closed by the stem 65; the hollow cylindrical element 60 of the upper receptacle 3, thanks mainly to its first circumferential wall 62, closes the peripheral area 52 of the transversal septum 40, where the transfer openings 51 are. In this way, even if the container according to the present invention were tilted or even turned upside down, the contents of the lower receptacle 2 would not flow back into the upper receptacle 3.

It should be understood that the main object of the invention has been achieved, namely that of creating a container for biological samples that allows a tight seal of the toxic liquid or considered as such. The individual components of the container can be made of any suitable material that cannot be passed through by liquids and gases, preferably a plastic material such as polypropylene, polyethylene terephthalate (PET), or combinations thereof.

The invention claimed is:

1. A container (1) for biologic samples, comprising:
- a lower receptacle (2), having a side wall (20) provided with a first external thread (21) and terminating with a first circular mouth (22),
- an upper receptacle (3) designed to contain, before activating the container (1), a toxic liquid (LF) or considered as such, having a side wall (30) being provided with a second external thread (31) and terminating at one end with a second circular mouth (32) and at the other end with a closed base (33);
- a connecting sleeve (4), comprising:
  - a lower part (41) having a lower side wall (43) with a first internal thread (44) engaging the first external thread (21) of the lower receptacle (2),
  - an upper part (42) having an upper side wall (45) terminating with a free end (46) and including a first internally smooth band (47), an internally threaded zone (48) with a thread (70) engaging the external thread (31) of the upper receptacle (3), and a second internally smooth zone (49) near the free end (46);

- a transversal septum (40) separating said lower part (41) from said upper part (42) and being provided with a central vent opening (55), made in a chimney element (65), and with a plurality of transfer openings (51) made, for a transfer of the toxic liquid (LF), in a peripheral area (52) with respect to the central vent opening (55), characterized in that
- in said connecting sleeve (4):
  - said peripheral area (52) of the transversal septum (40) is internally delimited by a first circumferential projection (53) orthogonally protruding in the upper part (42) of the connecting sleeve (4), the first circumferential projection (53) being adapted to create a tight seal with said second circular mouth (32), when the upper receptacle (3) is completely screwed into the upper part (42) of the connecting sleeve (4), and
  - a circumferential rim (54), being at least partial, projects inward near the free end (46) of the upper side wall (45), the circumferential rim (54) having an inner diameter adapted to create an undercut in said second internally smooth zone (49) in the upper part (42) of the connecting sleeve (4), and
- said upper receptacle (3) comprises, concentrically with said second circular mouth (32):
  - in said second internally smooth zone (49) near the free end (46) a radial ring (63) having an outer diameter greater than the internal diameter of said circumferential rim (54) of the connecting sleeve (4), and
  - a stem (56) leaning inwardly from said closed base (33) of the upper receptacle (3), the stem (56) being able to fit tightly into the central vent opening (55) of the transversal septum (40) when the upper receptacle (3) is completely screwed, and to create an air passage when the upper receptacle (3) is partially unscrewed up to said circumferential rim (54).

2. The container (1) according to claim 1, wherein said upper receptacle (3) comprises, concentrically with said second circular mouth (32), a hollow cylindrical element (60) having a transverse base (61) and a first circumferential longitudinal wall (62) intended to be tightly sealed in lateral contact with said first internally smooth band (47) of the upper side wall (45) of the connecting sleeve (4).

3. The container (1) according to claim 1, wherein a second circumferential projection (57) protrudes from the transversal septum (40) orthogonally in the upper part (42) of the connecting sleeve (4) so as to create a first groove (58) adapt to sealingly receive said second circular mouth (32) of the upper receptacle (3).

4. The container (1) according to claim 2, wherein a third circumferential projection (59) protrudes from the transversal septum (40) orthogonally in the upper part (42) of the connecting sleeve (4) so as to create a second groove (64) for sealingly receiving said first longitudinal circumferential wall (62) of the hollow cylindrical element (60) of the upper receptacle (3).

5. The container (1) according to claim 2, wherein said upper receptacle (3) comprises, concentrically with said second circular mouth (32), in its hollow cylindrical element (60) a second longitudinal circumferential wall (72) destined to come in end contact with said peripheral area (52) of the transversal septum (40) of the connecting sleeve (4).

6. The container (1) according to claim 1, wherein said upper receptacle (3) has the radial ring (63) and the external thread (31) both made flexible so as to allow a forced introduction of the upper receptacle (3) in the upper part (42) of the connecting sleeve (4).

7. The container (1) according to claim 1, wherein said transversal septum (40) has a recess (66) extending on its side opposite to that of said chimney element (65), recess (66) into which the central vent opening (55) of the chimney element (65) merges in a narrow port (67).

8. The container (1) according to claim 7, wherein said stem (56) of the upper receptacle (3), which is able to move in the central venting opening (55) of the chimney element (65) in screwing and unscrewing the upper receptacle (3) in the upper part (42) of the connecting sleeve (4), has a terminal tract (68) of reduced diameter with respect to that of the rest of the stem (56), terminal tract (68) which is able to provide:
 - a tight seal with said narrow port (67) of the central vent opening (55) in the recess (66) when the upper receptacle (3) is completely screwed into the upper part (42) of the connecting sleeve (4), and
 - a passage of air when the upper receptacle (3) is unscrewed in the upper part (42) of the connecting sleeve (4) up to the circumferential rim (54).

9. The container (1) according to claim 1, wherein the upper receptacle (3) has two opposite external radial fins (73) to facilitate a grip of the upper receptacle (3) for its rotation.

10. The container (1) according to claim 1, wherein the connecting sleeve (4) has a bulge (69) protruding outwards in its free end (46).

11. A method for the preservation of a biological sample by activating the container according to claim 1, comprising the steps of complete unscrewing the lower receptacle (2) from the connecting sleeve (4), directly inserting the biological sample inside the lower receptacle (2), re-screwing the lower receptacle (2) on the connecting sleeve (4) so as to obtain a tight seal, characterized by the following further steps:
 unscrewing the upper receptacle (3) until the contact of its radial ring (63) with the circumferential rim (54) of the connecting sleeve (4) so as to transfer the toxic liquid (LF) into the lower receptacle (2) through the plurality of transfer openings (51) in said peripheral area (52) of the transversal septum (40) and make the air contained in the lower receptacle (2) flow through the central vent opening (55) of the chimney element (65);
 tight re-screwing the upper receptacle (3) up to the stop of the second circular mouth (32) on the transversal septum (40),
so that,
 before activating the container (1), the toxic liquid (LF) is confined in a space delimited by the upper receptacle (3) and by the transversal septum (40), against which the upper receptacle (3) is completely screwed into the upper part (42) of the connecting sleeve (4),
 while activating the container (1), there is no communication of the inside of the container (1) with the outside, when unscrewing the upper receptacle (3), and
 after activating the container (1), the container (1) is closed again by screwing the upper receptacle (3) against the transversal septum (40) of the connecting sleeve (4), without any communication between the lower receptacle (2) and the upper receptacle (3).

12. The method according to claim 11, wherein the lower receptacle (2) is intended to contain, before activating the container (1), a non-toxic liquid (LS).

* * * * *